United States Patent
Tapinos et al.

(10) Patent No.: US 10,028,997 B2
(45) Date of Patent: Jul. 24, 2018

(54) SYSTEMS AND METHODS FOR ATTRACTING AND TRAPPING BRAIN CANCER CELLS

(71) Applicant: GEISINGER HEALTH SYSTEM, Danville, PA (US)

(72) Inventors: Nikolaos Tapinos, Barrington, RI (US); Atom Sarkar, Danville, PA (US); Margot Martinez-Moreno, Danville, PA (US)

(*) Notice: Subject to any disclaimer, the term of this patent is extended or adjusted under 35 U.S.C. 154(b) by 0 days.

(21) Appl. No.: 15/321,323

(22) PCT Filed: Jun. 4, 2015

(86) PCT No.: PCT/US2015/034159
§ 371 (c)(1),
(2) Date: Dec. 22, 2016

(87) PCT Pub. No.: WO2015/187925
PCT Pub. Date: Dec. 10, 2015

(65) Prior Publication Data
US 2017/0252401 A1    Sep. 7, 2017

Related U.S. Application Data

(60) Provisional application No. 62/007,595, filed on Jun. 4, 2014.

(51) Int. Cl.
| | | |
|---|---|---|
| A61K 47/42 | (2017.01) | |
| A61K 38/17 | (2006.01) | |
| A61K 9/06 | (2006.01) | |
| A61K 9/00 | (2006.01) | |
| A61K 31/495 | (2006.01) | |
| A61M 5/142 | (2006.01) | |

(52) U.S. Cl.
CPC ........ *A61K 38/1709* (2013.01); *A61K 9/0024* (2013.01); *A61K 9/06* (2013.01); *A61K 31/495* (2013.01); *A61K 47/42* (2013.01); *A61M 5/14276* (2013.01); *A61M 2202/0007* (2013.01); *A61M 2205/02* (2013.01); *A61M 2210/0693* (2013.01)

(58) Field of Classification Search
None
See application file for complete search history.

(56) References Cited

FOREIGN PATENT DOCUMENTS

WO    WO-2014063128 A1 *  4/2014  ........... A61L 31/041

OTHER PUBLICATIONS

International Search Report for PCT Patent App. No. PCT/US2015/034159 (dated Oct. 6, 2015).
Written Opinion for PCT Patent App. No. PCT/US2015/034159 (dated Oct. 6, 2015).
International Preliminary Report on Patentability for PCT Patent App. No. PCT/US2015/034159 (dated Dec. 15, 2016).

* cited by examiner

*Primary Examiner* — Fred H Reynolds
(74) *Attorney, Agent, or Firm* — Cermak Nakajima & McGowan LLP; Malcolm K. McGowan

(57) ABSTRACT

Described herein are systems and methods for attracting and trapping cancer cells at a specific site where focal radiation and/or surgical resection and/or chemotherapeutics can eliminate them.

18 Claims, 10 Drawing Sheets

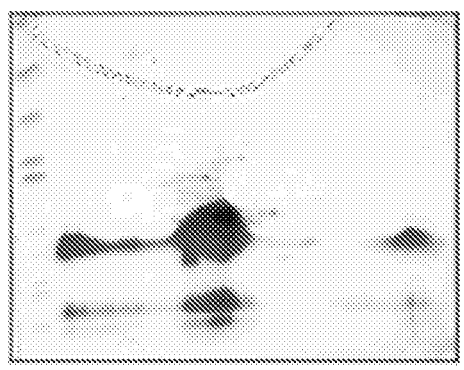
FIG. 1

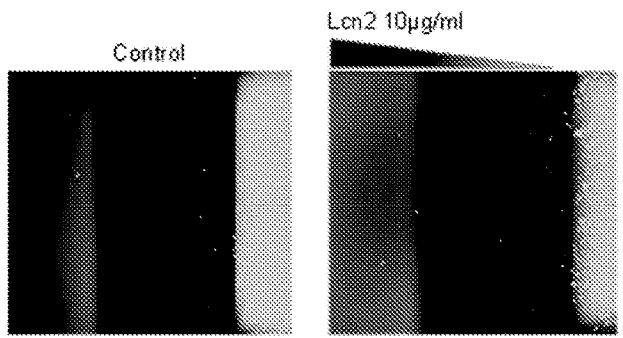
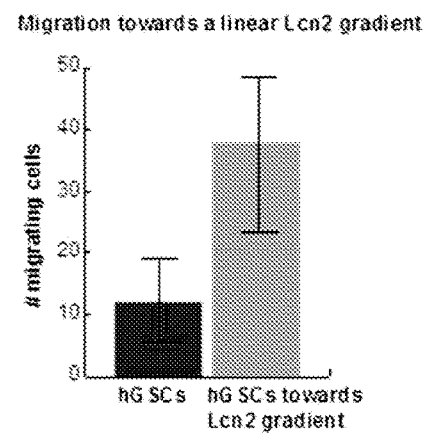
FIG. 4A
FIG. 4B
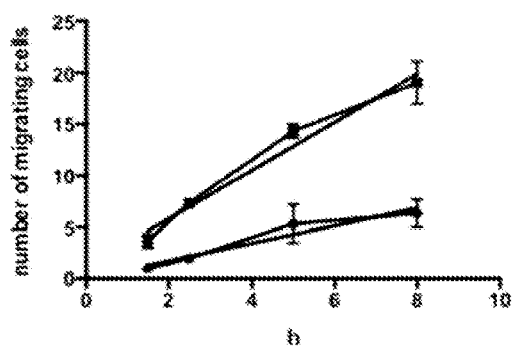
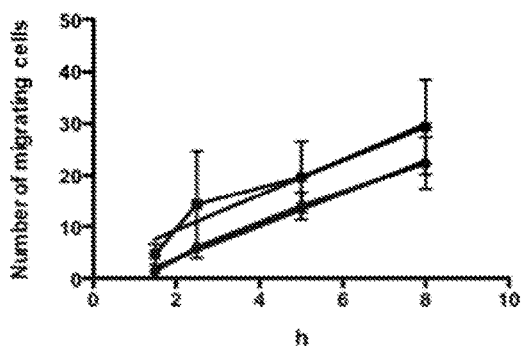
FIG. 4C

SEQ ID NO:1

MPLGLLWLGLALLGALHAQAQDSTSDLIPAPPLSKVPLQQNFQDNQFQGKWYVVG
LAGNAILREDKDPQKMYATIYELKEDKSYNVTSVLFRKKKCDYWIRTFVPGCQPGE
FTLGNIKSYPGLTSYLVRVVSTNYNQHAMVFFKKVSQNREYFKITLYGRTKELTSEL
KENFIRFSKSLGLPENHIVFPVPIDQCIDG

FIG. 5

SEQ ID NO:2

ACTCGCCACCTCCTCTTCCACCCCTGCCAGGCCCAGCAGCCACCACAGCGCCT
GCTTCCTCGGCCCTGAAATCATGCCCCTAGGTCTCCTGTGGCTGGGCCTAGCC
CTGTTGGGGGCTCTGCATGCCCAGGCCCAGGACTCCACCTCAGACCTGATCCC
AGCCCCACCTCTGAGCAAGGTCCCTCTGCAGCAGAACTTCCAGGACAACCAAT
TCCAGGGGAAGTGGTATGTGGTAGGCCTGGCAGGGAATGCAATTCTCAGAGAA
GACAAAGACCCGCAAAAGATGTATGCCACCATCTATGAGCTGAAAGAAGACAA
GAGCTACAATGTCACCTCCGTCCTGTTTAGGAAAAAGAAGTGTGACTACTGGAT
CAGGACTTTTGTTCCAGGTTGCCAGCCCGGCGAGTTCACGCTGGGCAACATTA
AGAGTTACCCTGGATTAACGAGTTACCTCGTCCGAGTGGTGAGCACCAACTACA
ACCAGCATGCTATGGTGTTCTTCAAGAAAGTTTCTCAAAACAGGGAGTACTTCA
AGATCACCCTCTACGGGAGAACCAAGGAGCTGACTTCGGAACTAAAGGAGAAC
TTCATCCGCTTCTCCAAATCTCTGGGCCTCCCTGAAAACCACATCGTCTTCCCT
GTCCCAATCGACCAGTGTATCGACGGCTGAGTGCACAGGTGCCGCCAGCTGCC
GCACCAGCCCGAACACCATTGAGGGAGCTGGGAGACCCTCCCCACAGTGCCA
CCCATGCAGCTGCTCCCCAGGCCACCCGCTGATGGAGCCCCACCTTGTCTGC
TAAATAAACATGCCCTCAGGCCAAAAAAAAAAAAAAAAAA

FIG. 6

SEQUENCE LISTING

<160> NUMBER OF SEQ ID NOS: 4

<210> SEQ ID NO 1
<211> LENGTH: 198
<212> TYPE: PRT
<213> ORGANISM: Homo sapiens

<400> SEQUENCE: 1

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195

<210> SEQ ID NO 2
<211> LENGTH: 840
<212> TYPE: DNA
<213> ORGANISM: Homo sapiens

<400> SEQUENCE: 2
actcgccacc tcctcttcca cccctgccag gcccagcagc caccacagcg cctgcttcct      60
cggccctgaa atcatgcccc taggtctcct gtggctgggc ctagccctgt tggggctct     120 gcatgcccag gcccaggact ccacctcaga cctgatccca gccccacctc tgagcaaggt     180
ccctctgcag cagaacttcc aggacaacca attccagggg aagtggtatg tggtaggcct     240
ggcagggaat gcaattctca gagaagacaa agacccgcaa aagatgtatg ccaccatcta     300
tgagctgaaa gaagacaaga gctacaatgt cacctccgtc ctgtttagga aaaagaagtg     360
tgactactgg atcaggactt ttgttccagg ttgccagccc ggcgagttca cgctgggcaa     420
cattaagagt taccctggat taacgagtta cctcgtccga gtggtgagca ccaactacaa     480
ccagcatgct atggtgttct tcaagaaagt ttctcaaaac agggagtact caagatcac     540 cctctacggg agaaccaagg agctgacttc ggaactaaag gagaacttca tccgcttctc     600
caaatctctg ggcctcccctg aaaaccacat cgtcttccct gtcccaatcg accagtgtat     660

-continued

```
cgacggctga gtgcacaggt gccgccagct gccgcaccag cccgaacacc attgagggag    720
ctgggagacc ctccccacag tgccacccat gcagctgctc cccaggccac cccgctgatg    780
gagccccacc ttgtctgcta aataaacatg tgccctcagg ccaaaaaaaa aaaaaaaaaa    840

<210> SEQ ID NO 3
<211> LENGTH: 22
<212> TYPE: DNA
<213> ORGANISM: Homo sapiens

<400> SEQUENCE: 3
aaattgagca cagcaccttt ga                                              22

<210> SEQ ID NO 4
<211> LENGTH: 24
<212> TYPE: DNA
<213> ORGANISM: Homo sapiens

<400> SEQUENCE: 4
tctgctttcc tgactcgaat aatg                                            24
```

SYSTEMS AND METHODS FOR ATTRACTING AND TRAPPING BRAIN CANCER CELLS

CROSS-REFERENCE TO RELATED APPLICATION

This application claims priority to U.S. Provisional Patent Application Ser. No. 62/007,595, filed on Jun. 4, 2014, which is incorporated herein by reference in its entirety for all purposes.

FIELD OF THE INVENTION

The present disclosure relates to systems and methods for attracting and trapping cancer cells at a specific site where focal radiation and/or surgical resection and/or chemotherapeutics can eliminate them.

BACKGROUND

One of the most frustrating facets of cancer biology is that secondary tumor metastases can lie dormant until activated by a suitable stimulus. This stimulus is often the surgical removal of a primary tumor. Primary tumors secrete antiangiogenic factors that decrease angiogenesis in secondary tumors, and thereby inhibit their growth. See, e.g., Sckell et al., CANCER RESEARCH 58:5866-5869 (1998) and Guba et al., CANCER RESEARCH 61:5575-5579 (2001). Removal of the primary tumor withdraws these antiangiogenic inhibitors and allows the secondary tumors to proliferate.

Inducing primary and secondary tumor cells to migrate towards a source of chemoattractant could be used as a means to isolate an invasive cell population. This would be especially effective for the treatment of glioblastoma, the most aggressive and universally fatal human brain tumor.

Every year 15,000 new cases of glioblastoma are diagnosed in the United States. More than 75% of these patients will die within two years following their initial diagnosis, even after administration of the standard triple therapy of surgical resection, radiation, and chemotherapy. See, e.g., Stupp et al., ONKOLOGIE 28(6-7):315-7 (2005).

Current treatment of glioblastoma includes surgical resection of the tumor mass followed by radiation in the vicinity of the resection cavity (usually 1-2 cm around) (Stupp et al., THE NEW ENGLAND JOURNAL OF MEDICINE 352(10):987-96 (2005)) and administration of temozolomide (Stupp et al., ONKOLOGIE 28(6-7):315-7 (2005)). Even with this multi-therapeutic approach, tumor recurrence is inevitable (Wick et al., NEURO-ONCOLOGY 13(6):566-79 (2011)). This is due to the migration properties of the tumor cells, which invade the brain parenchyma creating multiple finger-like projections within the brain (Friedl et al., NATURE REVIEWS CANCER 3(5): 362-74 (2003)) that make their elimination virtually impossible. It is evident that even after decades of intense clinical and basic research an efficient treatment for glioblastoma does not exist and a diagnosis of glioblastoma is still a terminal diagnosis.

Methods for isolating and sequestering motile cells have been described. U.S. Patent Application Publication No. 2013/0172846 to Bellamkonda et al. relates to a device having one or more surface structures which provide physical guidance cues for directing the migration of tumor cells from a first tissue location to a selected second location. U.S. Patent Application Publication No. 2011/0020216 to Mooney et al. pertains to a device capable of capturing, and therefore sequestering, undesirable cells, either within an internal compartment or along its external surface by either filtering cells through pores in the external surface or binding cells to adhesive proteins along either its internal or external surfaces. U.S. Patent Application Publication No. 2010/0124573 to Naughton et al. relates to methods of using extracellular matrix (ECM) compositions for the inhibition of growth or proliferation of cancers alone or as a biological vehicle for the delivery of a chemotherapeutic agent. U.S. Patent Application Publication No. 2012/0322685 to Condeelis et al. pertains to a method of isolating motile cells from an animal tissue comprising implanting in the animal tissue a cell trap comprising at least one chamber with an inlet for ingress of motile cells, and a porous matrix located in the chamber comprising a chemotactic factor, for a time sufficient for the motile cells to migrate into the cell trap, removing the implanted cell trap, and retrieving the motile cells from the cell trap. Williams et al., PROCEEDINGS OF SPIE 8251:1-7 (2012), pertains to an optically transparent, implantable tool to study the tumor microenvironment loaded with a hydrogel that is implanted into a tumor. Wang et al., BIOMATERIALS 30(36):6986-95 (2009) pertains to an immunocyte delivery platform with which cell-based immunotherapy can be initiated at a desired location and implemented in a controlled manner. However, these methods suffer from several disadvantages, including non-biocompatibility of physical devices and lack of effective chemoattractants.

Accordingly, described herein are new systems and methods for attracting and trapping brain cancer cells that are safer and more effective than currently-available modalities.

SUMMARY OF THE DISCLOSURE

In one embodiment, a method for attracting and trapping cancer cells comprising implanting a composition comprising a chemoattractant into a subject in need thereof and removing any cancer cells that have migrated adjacent to the composition is disclosed. In another embodiment, the chemoattractant attracts brain cancer cells. In another embodiment, the chemoattractant is at least 95% identical to SEQ ID NO:1. In another embodiment, the chemoattractant is a cDNA encoding the amino acid sequence of SEQ ID NO:1. In another embodiment, the cDNA is SEQ ID NO:2. In another embodiment, the composition is selected from the group consisting of a biodegradable hydrogel, a biodegradable scaffold, a biodegradable polymer microsphere, and mixtures thereof. In another embodiment, the composition is an implantable drug delivery pump.

In another embodiment, a method for attracting and trapping cancer cells comprising implanting a composition comprising a chemoattractant into a subject in need thereof and removing any cancer cells that have migrated adjacent to the composition is disclosed wherein the cancer cells are removed via surgical resection and/or destroyed via focal radiation. In another embodiment, the chemoattractant is released for approximately 1-2 weeks before the cancer cells are removed. In another embodiment, the chemoattractant is present in an amount of about 1 mg.

In another embodiment, a composition comprising a chemoattractant and a chemotherapeutic agent is disclosed wherein the composition is formulated in a manner such that the chemoattractant is released prior to the chemotherapeutic agent. In another embodiment, the composition is formulated to be implanted in a subject in need thereof. In another embodiment, the chemotherapeutic agent is selected from the group consisting of temozolomide, cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, folinic acid, and oxaliplatin. In another embodiment, the chemotherapeutic agent is temozolomide. In another embodiment, the temozolomide is present in an amount of about 200 mg/m$^2$. In another embodiment, the chemoattractant attracts brain cancer cells. In another embodiment, the chemoattractant is at least 95% identical to SEQ ID NO:1. In another embodiment, the chemoattractant is a 39 amino acid peptide fragment of the sequence of SEQ ID NO:1. In another embodiment, the chemoattractant is a cDNA encoding the amino acid sequence of SEQ ID NO:1. In another embodiment, the cDNA is SEQ ID NO:2. In another embodiment, the chemoattractant is a cDNA encoding a 39 amino acid peptide fragment of the sequence of SEQ ID NO:1. In another embodiment, the chemoattractant is released for approximately 1-4 weeks before the chemotherapeutic agent is released.

In another embodiment, a method for attracting and trapping cancer cells is disclosed comprising implanting a composition comprising a chemoattractant and a chemotherapeutic agent into a subject in need thereof wherein the composition is formulated in a manner such that the chemoattractant is released prior to the chemotherapeutic agent. In another embodiment, a method for treating cancer is disclosed comprising implanting an effective amount of composition comprising a chemoattractant and a chemotherapeutic agent into a subject in need thereof wherein the composition is formulated in a manner such that the chemoattractant is released prior to the chemotherapeutic agent. In another embodiment, a method for treating cancer is disclosed comprising identifying a subject whose cancer cells express a lipocalin-2 receptor and implanting a composition comprising a chemoattractant and a chemotherapeutic agent into the subject in need thereof wherein the composition is formulated in a manner such that the chemoattractant is released prior to the chemotherapeutic agent.

In another embodiment, a composition comprising a chemoattractant and a chemotherapeutic agent is disclosed wherein the composition is formulated as a biodegradable biphasic-release hydrogel. In another embodiment, the hydrogel comprises two multifunctional polyols that possess thiol functionality and one multifunctional polyol that contains acrylate functionality.

BRIEF DESCRIPTION OF DRAWINGS

FIG. 1: A 2-D electrophoresis comparison of spent medium from human neural stem cells (left panel; "Control media") and spent medium from human glioblastoma stem cells (right panel; "GBM stem cell media").

FIG. 2C is a chart that shows that lipocalin-2 significantly increased the rate of migration of human glioblastoma stem cells (hGSCs).

FIGS. 4A-C: Human glioblastoma stem cells (hGSCs) migrate toward a stable linear lipocalin-2 (Lcn2) gradient (A). The number of migrating human glioblastoma stem cells (hGSCs) were counted in the presence and absence of a lipocalin-2 gradient (B, C) to demonstrate that lipocalin-2 has a chemotactic effect as opposed to a chemokinetic effect.

FIG. 5: The amino acid sequence for lipocalin-2 (SEQ ID NO:1), Protein Accession Number: P80188.

FIG. 6: The cDNA sequence for lipocalin-2 (SEQ ID NO:2), NCBI Reference Sequence: NM_005564.3, GI:108936956.

DETAILED DESCRIPTION OF THE INVENTION

Figure 2A:
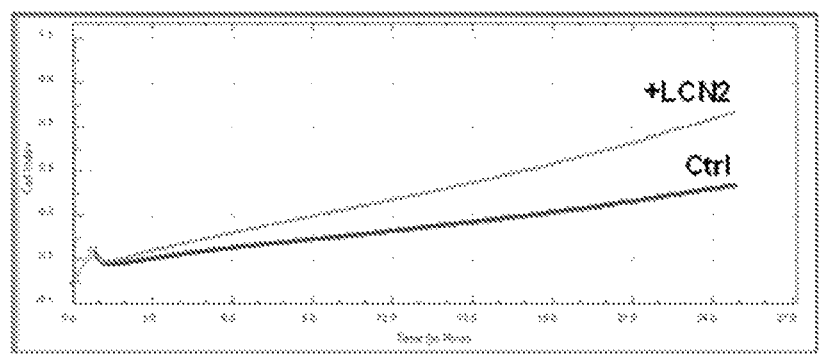
FIGS. 2A-2C: A comparison of the migration of human glioblastoma stem cells (hGSCs) seeded on the top chamber of a CIM XCELLIGENCE® plate in the presence of 10 µg/ml lipocalin-2 (grey line; "+LCN2") or serum alone (black line; "Ctrl") (A). A comparison of the migration of human glioblastoma stem cells (hGSCs), pretreated with lipocalin-2, seeded on the top chamber of a CIM XCELLIGENCE® plate in the presence or absence of lipocalin-2 in the bottom Boyden chamber (B).

As used herein, the terms "condition," "disease," and "disorder" are used interchangeably.

A "subject" to which administration is contemplated includes, but is not limited to, humans (i.e., a male or female of any age group, e.g., a pediatric subject (e.g., infant, child adolescent) or adult subject (e.g., young adult, middle-aged adult, or senior adult)) and/or other non-human animals, for example, mammals (e.g., rodents (e.g., mice, rats, guinea pigs, hamsters), primates (e.g., cynomolgus monkeys, rhesus monkeys); commercially-relevant mammals such as cattle, pigs, horses sheep, goats, cats, and/or dogs) and birds (e.g., commercially relevant birds such as chickens, ducks, geese, and/or turkeys). The animal may be a male or female at any stage of development. A non-human animal may be a transgenic animal.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

An "effective amount" of the described composition refers to an amount sufficient to elicit a biological response, i.e., treating the condition. As will be appreciated by those of ordinary skill in the art, the effective amount may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effect amount of the composition may reduce the tumor burden or stop the growth or spread of a tumor by eliminating cancerous cells.

As used herein, the terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," metastatic," or "metastasize" refers to the spread or migration of cancerous cells from a primary or original tumor to another organ or tissue and is typically identifiable by the presence of a "secondary tumor" or secondary cell mass" of the tissue type of the primary or original tumor and not of that of the organ or tissue in which the secondary (metastatic) tumor is located. For example, a breast cancer that has migrated to the lungs is said to be metastasized breast cancer and includes cancerous breast cancer cells growing in lung tissue. In the case of glioblastomas, which are the most aggressive primary brain tumors in humans, the tumor cells migrate within the brain and these migrating cells eventually develop recurrent tumors soon after the seeming eradication of the primary tumor.

As used herein, the term "cancer" refers to a malignant neoplasm (*Stedman's Medical Dictionary*, 25$^{th}$ ed.; Hensyl ed.; Williams & Wilkins: Philadelphia, 1990). An exemplary cancer is, but is not limited to, brain cancer (e.g., meningioma, glioblastomas, glioma (e.g., astrocytoma, oligodendroglioma), medulloblastoma).

A "biocompatible" material refers to a material that does not typically induce an adverse response when inserted or injected into a subject. The adverse response includes significant inflammation and/or acute rejection of the material by the immune system of the subject, for instance, via a T-cell-mediated response. It is recognized that "biocompatibility" is a relative term and that some degree of immune response is to be expected even for materials that are highly compatible with living tissues of the subject. However, as used herein, "biocompatibility" refers to the acute rejection of a material by at least a portion of the immune system, i.e., a material that lacks biocompatibility (i.e., being non-biocompatible) in a subject provokes an immune response in the subject that is severe enough such that the rejection of the material by the immune system cannot be adequately controlled and often is of a degree such that the material must be removed from the subject in order for the subject to be as well as it was before the non-biocompatible material was introduced into the subject. One test to determine biocompatibility of a material is to expose the material to cells (e.g., fibroblasts or epithelial cells) in vitro; the material is considered biocompatible if it does not result in significant cell death at moderate concentrations, e.g., at concentrations of about 50 micrograms/$10^6$ cells. In certain embodiments, there is no significant cell death if less than about 20% of the cells are dead, even if phagocytosed or otherwise taken up by the cells. In some embodiments, a material is biocompatible if contacting it with cells in vitro results in less than 20% cell death and if the administration of the material in vivo does not induce unwanted inflammation or other adverse responses. In certain embodiments, a biocompatible material is biodegradable. A non-limiting example of a biocompatible material is a biocompatible polymer (including biocompatible copolymers).

A "biodegradable" material refers to a material that is able to degrade chemically and/or biologically (e.g., by hydrolysis or enzymatic activity) within a physiological environment, such as within the body or when introduced to cells. For instance, the material may be one that hydrolyzes spontaneously upon exposure to water (e.g., within a subject) and/or may degrade upon exposure to heat (e.g., at temperatures above 37° C.). Degradation of a material may occur at varying rates, depending on the material used. For example, the half-life of the material (the time at which 50% of the material is degraded into smaller components) may be on the order of days, weeks, months, or years. The material may be biologically degraded, e.g., by enzymatic activity or cellular machinery, for example, through exposure to a lysozyme. In some embodiments, the material may be broken down into smaller components that cells can either reuse or dispose of without significant toxic effect on the cells (e.g., fewer than about 20% of the cells are killed when the components are added to cells in vitro). Non-limiting examples of biodegradable materials are biodegradable polymers (including biodegradable copolymers). Examples of biodegradable polymers include, but are not limited to, poly(ethylene glycol)-poly(propylene oxide)-poly(ethylene glycol) triblock copolymers, poly(vinyl alcohol) (PVA), poly(lactide) (or poly(lactic acid)), poly(glycolide) (or poly (glycolic acid)), poly(orthoesters), poly(caprolactones), polylysine, poly(ethylene imine), poly(acrylic acid), poly (urethanes), poly(anhydrides), poly(esters), poly(trimethylene carbonate), poly(ethyleneimine), poly(acrylic acid), poly(urethane), poly(beta amino esters), and copolymers thereof (e.g., poly(lactide-co-glycolide) (PLGA)).

As used herein, the term chemoattractant refers to a factor which attracts cells towards it, for example, lipocalin-2, epidermal growth factor, CSF-1, CCLx, ETs1-2, Lps, SDF-1, HGF, PDGF BIB, FGF-1, VEGF-α, Heregulin, TGF-α, or fetal serum. Preferably, the chemoattractant will attract cancer cells. Most preferably, motile cancer cells will move up the gradient of the chemoattractant and not down the chemoattractant gradient. When the motile cells of interest are brain cancer cells, lipocalin-2 is the preferred chemoattractant.

In one embodiment, the chemoattractant is lipocalin-2 (Lcn2). Lcn2 is a member of the lipocalin family, which binds or transports lipid and other hydrophobic molecules. See, e.g., Flower et al., BIOCHIMICA ET BIOPHYSICA ACTA 1482 (1-2):9-24 (2000), and Kjeldsen et al., BIOCHIMICA ET BIOPHYSICA ACTA 1482(1-2):272-83 (2000). Lcn2 is also known as 24p3 and neutrophil gelatinase associated lipocalin (NGAL). See Borregaard and Cowland, BIOMETALS 19(2):211-5 (2006). Lcn2 has been associated with breast cancer progression. In a study analyzing the plasma proteome, Lcn2 levels were increased in breast tumor-bearing transgenic mice compared to normal littermates and its levels further increased with tumor progression (Pitteri et al., THE JOURNAL OF PROTEOME RESEARCH 7(4):1481-9 (2008)). In human studies, Lcn2 expression was found to be associated with estrogen receptor-negative status in breast cancer cell lines and in breast cancer tissues (Stoesz et al., THE INTERNATIONAL JOURNAL OF CANCER 79(6):565-72 (1998); Gruvberger et al., CANCER RESEARCH 61(16):5979-84 (2001)). Lcn2 levels in breast cancer tissue also strongly correlate with characteristics that are associated with poor prognosis, including poor histologic grade, lymph node metastasis and high proliferation (Bauer et al., BREAST CANCER RESEARCH AND TREATMENT 108(3): 389-97 (2008)). Not surprisingly, it has also been shown to be an independent prognostic marker for decreased survival (Bauer et al., BREAST CANCER RESEARCH AND TREATMENT 108(3): 389-97 (2008)). Finally, Lcn2 is critical for cell death sensitization, stimulation of cell migration, and morphological changes of reactive astrocytes (Lee et al., THE JOURNAL OF NEUROSCIENCE 29(1):234-49 (2009)).

In certain embodiments, the chemoattractant is at least 70%, at least 75%, at least 80%, at least 85%, at least 90%, at least 95%, at least 98%, or at least 99% identical to SEQ ID NO:1. In another embodiment, the chemoattractant is SEQ ID NO:1. In other embodiments, the chemoattractant is a 39, 40, 50, 60, 70, 80, 90, 100, 110, 120, 130, 140, 150, 160, 170, 180, or 190 amino acid peptide fragment of the sequence of SEQ ID NO:1. In other embodiments, the chemoattractant is a peptide fragment spanning amino acids 1-40, 40-80, 80-120, 120-160, 160-198, 1-80, 1-120, 1-160, 120-198, 80-198, or 40-198 of the sequence of SEQ ID NO:1. In other embodiments, the chemoattractant is a cDNA encoding an amino acid sequence at least 70%, at least 75%, at least 80%, at least 85%, at least 90%, at least 95%, at least 98%, or at least 99% identical to SEQ ID NO:1. In another embodiment, the cDNA is SEQ ID NO:2. In other embodiments, the chemoattractant is a cDNA encoding a 39, 40, 50, 60, 70, 80, 90, 100, 110, 120, 130, 140, 150, 160, 170, 180, or 190 amino acid peptide fragment of the sequence of SEQ ID NO:1. In other embodiments, the chemoattractant is a cDNA encoding a peptide fragment spanning amino acids 1-40, 40-80, 80-120, 120-160, 160-198, 1-80, 1-120, 1-160, 120-198, 80-198, or 40-198 of the sequence of SEQ ID NO:1.

In certain embodiments, an effective amount of a chemoattractant for administration to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 100 mg, about 0.1 mg to about 10 mg, about 0.1 mg to about 2 mg, about 0.5 mg to about 5 mg, about 0.5 mg to about 1.5 mg, or about 1 mg to about 1.5 mg of a compound per unit dosage form. In other embodiments, an effective amount of a chemoattractant for administration may comprise about 0.0001, 0.001, 0.01, 0.1, 1, 2, 5, 10, 25, 50, 100, 250, 500, 750, 1000, 1500, 2000, 2500, or 3000 mg.

As used herein, the term chemotherapeutic agent refers to a chemical or chemicals useful for the treatment of cancer. Examples of chemotherapeutic agents include anti-proliferative or anti-neoplastic agents that inhibit cell division and/or DNA synthesis, and can include alkylating agents, anti-metabolites, anti-microtubule agents, topoisomerase inhibitors, and cytotoxic antibiotics. Common combination chemotherapy regimens include cyclophosphamide, methotrexate, and 5-fluorouracil for breast cancer; doxorubicin and cyclophosphamide for breast cancer; mustine, vincristine, procarbazine, and prednisolone for Hodgkin's disease; doxorubicin, bleomycin, vinblastine, and dacarbazine for Hodgkin's disease; cyclophosphamide, doxorubicin, vincristine, and prednisolone for Non-Hodgkin's lymphoma; bleomycin, etoposide, and cisplatin for germ cell tumors; epirubicin, cisplatin, and 5-fluorouracil for stomach cancer; epirubicin, cisplatin, and capecitabine for stomach cancer; methotrexate, vincristine, doxorubicin, and cisplatin for bladder cancer; cyclophosphamide, doxorubicin, and vincristine for lung cancer; and 5-fluorouracil, folinic acid, and oxaliplatin for colorectal cancer. Additional chemotherapeutic agents can be used based upon their effectiveness against a particular cancer type.

In one embodiment, the chemotherapeutic agent is a [3H]imidazo[5,1-d]1,2,3,5-tetrazin-4-one derivative, such as temozolomide and analogs thereof (including pharmaceutically acceptable salts and prodrugs thereof). Such compounds are known. See, e.g., U.S. Pat. Nos. 6,096,724; 6,844,434; and 5,260,291. One chemical name for temozolomide is 4-methyl-5-oxo-2,3,4,6,8-pentazabicyclo[4.3.0] nona-2,7,9-triene-9-carboxamide. Other names for temozolomide are TEMODAR, TEMODAL, and TEMCAD.

In certain embodiments, an effective amount of a chemotherapeutic for administration to a 70 kg adult human may comprise about 1 $mg/m^2$ to about 500 $mg/m^2$, about 10 $mg/m^2$ to about 400 $mg/m^2$, about 50 $mg/m^2$ to about 300 $mg/m^2$, about 100 $mg/m^2$ to about 300 $mg/m^2$, about 150 $mg/m^2$ to about 250 $mg/m^2$, or about 200 $mg/m^2$ to about 250 $mg/m^2$ of the patient's body surface area of a compound per unit dosage form. Other non-limiting examples of an effective amount of a chemotherapeutic agent include an amount ranging from about 10 $mg/m^2$ to about 500 $mg/m^2$, from about 20 $mg/m^2$ to about 250 $mg/m^2$, from about 50 $mg/m^2$ to about 100 $mg/m^2$, from about 10 $mg/m^2$ to about 250 $mg/m^2$, from about 10 $mg/m^2$ to about 100 $mg/m^2$, from about 10 $mg/m^2$ to about 50 $mg/m^2$, from about 20 $mg/m^2$ to about 500 $mg/m^2$, from about 50 $mg/m^2$ to about 500 $mg/m^2$, from about 100 $mg/m^2$ to about 500 $mg/m^2$, or from about 250 $mg/m^2$ to about 500 $mg/m^2$ of the patient's body surface of a compound per unit dosage form. Finally, further non-limiting examples of an effective amount of a chemotherapeutic agent include about 1, 2.5, 5, 10, 20, 25, 50, 100, 150, 200, 250, 300, 350, 400, 450, or 500 $mg/m^2$ of the patient's body surface area of a compound per unit dosage form.

As used herein, the term surgical resection refers to a surgical procedure to remove part of an organ or structure, such as a mass of tumor cells. A craniotomy is typically indicated for brain tumors so that the tumor can be removed and/or reduced in size. Resection can be performed via a resecting device, such as a cutting device or a suction device. As used herein, the term focal radiation refers to treatment using external beams, such as photon or proton beams. Focal radiation can be delivered via advanced radiosurgery delivery methods such as GAMMA KNIFE (Elekta, Stockholm, Sweden), CYBERKNIFE (Accuray Inc., Sunnyvale, Calif.), and the TRILOGY SYSTEM (Varian, Palo Alto, Calif.).

In one embodiment, the system comprises a locally injectable composition that has the capacity to both: (i) attract tumor cells to itself through the release of lipocalin-2 (Lcn2) and (ii) destroy these cells once they have made sufficient contact with the system. This destruction can be accomplished via local irradiation or by using a small molecule hydrophobic chemotherapeutic agent such as temozolomide.

In order to achieve effective modulation of cancer cell migration locally following resection of the primary tumor, the establishment of spatial gradients of lipocalin-2 (Lcn2) within the local microenvironment may be required. This gradient can persist for a period of time that is sufficient to force the movement of the entire residual tumor cell population toward the desired target. This period of time can be, e.g., 1-2 weeks, 2-4 weeks, or 1-4 weeks. To eliminate these cells once they have reached this target, effective long-term storage and then local controlled release of a chemotherapeutic agent can be obtained via a biphasic, biodegradable hydrogel.

In another embodiment, the system comprises a locally injectable biodegradable hydrogel that has the capacity to attract tumor cells to itself through the release of lipocalin-2 (Lcn2). The tumor cells can then be destroyed via focal radiation and/or removed via surgical resection once they have made sufficient contact with the system.

In another embodiment, the system comprises a locally injectable biodegradable scaffold that has the capacity to attract tumor cells to itself through the release of lipocalin-2 (Lcn2). The scaffolds can be formed out of suitable materials such as collagen, fibrin, chitosan, glycosaminoglycans (such as hyaluronic acid), poly(lactic acid), polyglycolic acid, and polycaprolactone. The tumor cells can then be destroyed via focal radiation and/or removed via surgical resection once they have made sufficient contact with the system.

In another embodiment, the system comprises a locally injectable polymer microsphere, such as a poly(lactic-co-glycolic acid) (PLGA) microsphere that has the capacity to attract tumor cells to itself through the release of lipocalin-2 (Lcn2). The tumor cells can then be destroyed via focal radiation and/or removed via surgical resection once they have made sufficient contact with the system.

In another embodiment, the system comprises an implantable drug delivery pump that has the capacity to attract tumor cells to itself through the release of lipocalin-2 (Lcn2). Examples of implantable drug delivery pumps include the ISOMED and SYNCHROMED implantable pumps (Medtronic, Inc., Minneapolis, Minn.). The tumor cells can then be destroyed via focal radiation and/or removed via surgical resection once they have made sufficient contact with the system.

EXAMPLES

In order that this disclosure may be more fully understood, the following examples are set forth. It should be understood that these examples are for illustrative purposes only and are not to be construed as limiting this invention in any manner.

Example 1

Identification of Lipocalin-2

Human glioblastoma stem cells (hGSCs) were isolated and expanded in vitro from patients with primary glioblastoma that underwent surgical resection. The spent medium from hGSCs and from normal human neural stem cells was collected and centrifuged to remove cellular debris. The media was analyzed by two-dimensional gel electrophoresis (FIG. 1). The differentially expressed dots were isolated and the proteins identified by mass spectrometry (ALPHAL-YSE). This analysis identified that lipocalin-2 is secreted by hGSCs (FIG. 1, right panel, red rectangle).

Example 2

The Effect of Lipocalin-2 on Migration

Figure 3A:
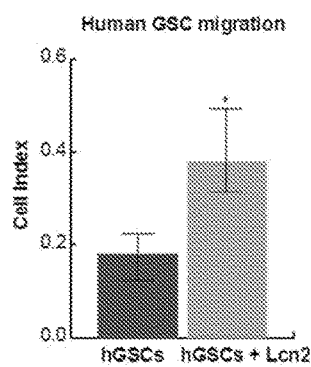
FIGS. 3A-C: A lipocalin-2 depot significantly increases the rate of migration of human glioblastoma stem cells (hGSCs) (A). The application of lipocalin-2 to just one Boyden chamber increases the rate of migration of human glioblastoma stem cells (hGSCs) to the lipocalin-2-containing chamber as opposed to when PBS is applied to one of the Boyden chambers or when lipocalin-2 is applied to both Boyden chambers (B, C). The number of migrating human glioblastoma stem cells (hGSCs) is lower when denatured lipocalin-2 is applied to one of the Boyden chambers (C).

Human glioblastoma stem cells (hGSCs) were seeded in an XCELLIGENCE RTCA CIM-16 plate, which functions as a Boyden chamber, in serum-free media. The XCELLIGENCE system (ACEA BIOSCIENCES, INC.) measures total surface area covered by cell membrane by detecting the electrical impedance, using microelectronic biosensor technology (Ness et al., NATURE COMMUNICATIONS 4:1912 (2013)). The lower chamber was supplemented with 10 μg/ml Lcn2 or 10% serum. Cell migration from the upper to the lower chamber was measured and plotted over time and the migration slope was calculated using RTCA DP software (ACEA BIOSCIENCES, INC.). The experiment was repeated four times and the results are presented as average+/−standard deviation. Lcn2 increases the migration of hGSCs as compared to serum alone (FIG. 2A) and significantly attracts hGSCs toward the bottom chamber that contains the Lcn2 depot (FIG. 3A). To demonstrate in vitro that hGSCs increase their chemotaxis towards a Lcn2 linear gradient, a chemotaxis assay plate (BELLBROOK LABS) was used to form a linear gradient of 10 μg/ml Lcn2 for 8 hours. hGSCs labeled green with CELLTRACKER exhibited increased migration toward the linear Lcn2 gradient (chemotaxis) while no difference in migration towards the opposite direction (chemokinesis) was detected (*p<0.005, FIGS. 4A-C).

Figure 2B:
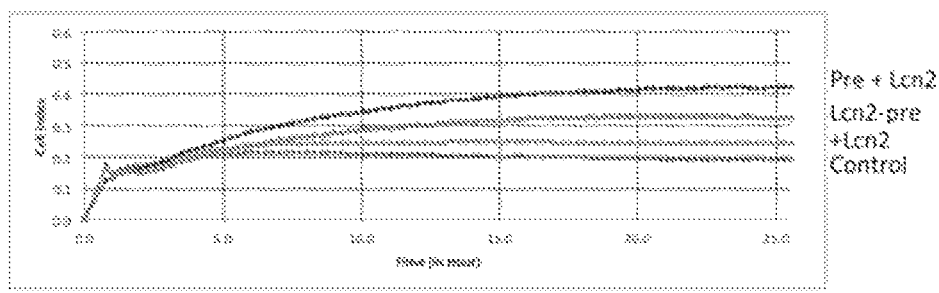
Figure 2C:
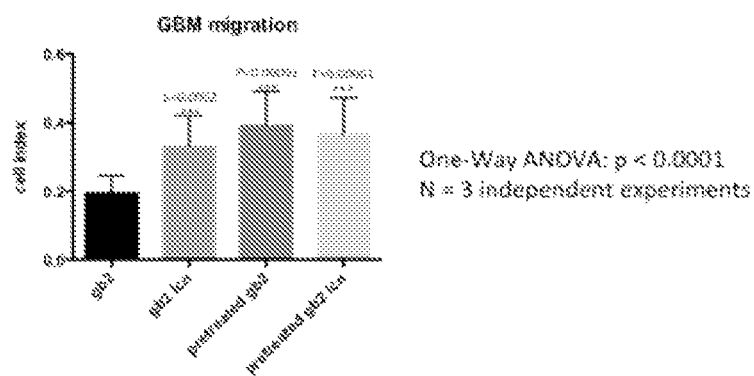

To further determine the effect of Lcn2 on glioblastoma cell migration, glioblastoma cells were first pre-treated with 10 μg/ml Lcn2 for 24 hours. Migration was subsequently quantified using the XCELLIGENCE system in the presence or absence of Lcn2 as a chemo-attractant in the lower Boyden chamber. Pre-treatment of human glioblastoma cells with Lcn2 induced a significant increase in migration (p<0.0001, FIGS. 2B and 2C). This observation suggested that exposure of human glioblastoma cells to Lcn2 in the vicinity of a tumor site increases the migration properties of these cells contributing to enhanced metastatic potential.

Figure 3B:
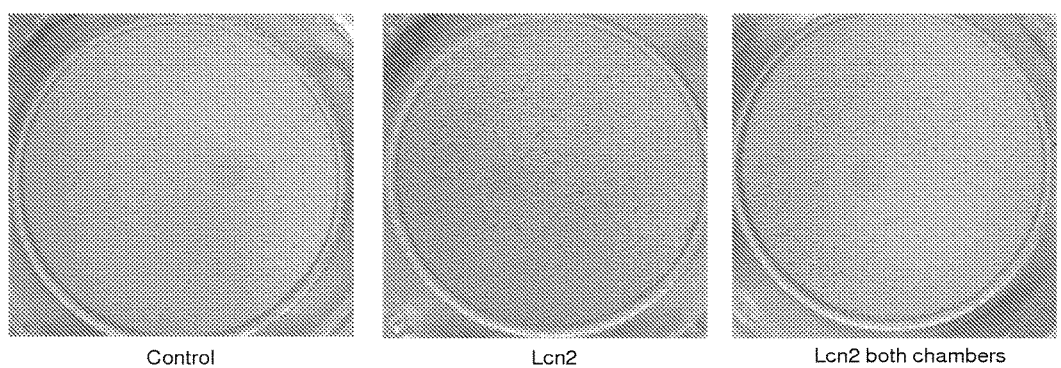
Figure 3C:
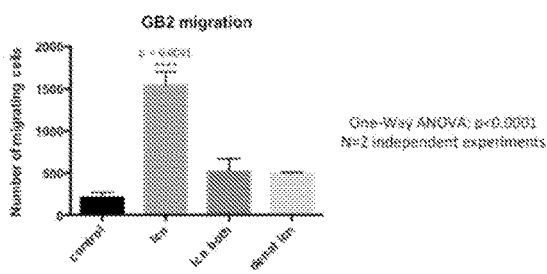

Finally, human glioblastoma cell migration was also observed under the microscope. hGSCs were seeded in the upper Boyden chamber in serum free medium. Lcn2 was added to the bottom chamber at 10 μg/ml and cells were allowed to migrate for 16 hours. The bottom chamber was fixed and stained with crystal violet and cells were counted using a Zeiss Phase Contrast microscope at 10× magnification. When Lcn2 was added to the bottom chamber, a significant increase in hGSC migration was observed (FIGS. 3B and 3C, p<0.0001). To show the specificity of the Lcn2 chemotactic effect and to determine if the effect of Lcn2 on migration is sequence dependent, Lcn2 was denatured by boiling in SDS buffer for 10 minutes and then added to the bottom Boyden chamber. No effect on hGSC migration was observed, demonstrating the specificity of Lcn2 and suggesting that the binding of Lcn2 to its cell surface receptor is structure dependent (FIG. 3C).

Example 3

Manipulation of Lipocalin-2 Levels

Human glioblastoma stem cells (hGSCs) are pre-incubated overnight with 10 µg/ml Lcn2 as previously shown (Lee et al., THE JOURNAL OF NEUROSCIENCE 29(1):234-49 (2009)) to evaluate the continuous effect of Lcn2 on the rate of GSC migration using the XCELLIGENCE CIM plates. The expression and secretion of Lcn2 is inhibited with siRNAs and migration of hGSCs on the XCELLIGENCE system is examined. In addition, GFP-expressing hGSCs with or without Lcn2 siRNAs are plated on rat dorsal root ganglion neurons and their migration along axonal tracks is monitored with live cell imaging (ZEISS) as demonstrated before (Ness et al., NATURE COMMUNICATIONS 4:1912 (2013)). Additionally, the effect of Lcn2 inhibition on hGSC migration signaling pathways is studied via western blotting and immunoprecipitations to determine the activation state of paxilllin, Rho/ROCK and Rac1 in hGSC lysates after inhibition of Lcn2 expression with siRNAs.

Example 4

Formulation of a Lipocalin-2 Biodegradable Hydrogel

Lipocalin-2 (Lcn2) formulated into a two stage release biodegradable hydrogel allows initial diffusion of Lcn2 (a 23 kDa hydrophilic protein) for approximately 1-2 weeks followed by a delayed but also sufficiently controlled diffusion of the much smaller chemotherapeutic temozolomide (194 Da). To establish this required two-phase release profile for Lcn2 and temozolime within the enclosed confines of the brain, a biodegradable non-swelling hydrogel is used that comprises three multifunctional ethoxylated polyols (small molecular weight PEG oligomers); two that possess thiol functionality and one that contains acrylate functionality. One of the thiol functionalized ethoxylated polyols is an amphiphilic molecule that allows for the creation of micellular microstructure within the hydrogel that is used to partition and encapsulate the hydrophobic temozolomide. The remaining two molecules react to create the hydrogel network as well as integrate the thiol functionalized temozolomide micelles within it to form a single uniform material. By solubilizing Lcn2 within a solution of hydrogel precursors, upon gelation this protein is suspended uniformly throughout the hydrogel where the effective polymeric mesh acts as a barrier for controlling molecular diffusion.

A library of unique biphasic hydrogel materials with diverse dual drug release profiles are formed by leveraging a number of unique thiol and acrylate ethoxylated polyols precursors with minor variations in chemistry. Using in vitro hydrogel incubation assays, the release kinetics of both Lcn2 and temozolomide from single hydrogel formulations is characterized. For Lcn2 quantification a QUANTIKINE ELISA (R&D SYSTEMS) is used. Temozolomide concentrations are characterized by organic extraction and high performance liquid chromatography (HPLC) according to established protocol (Kim et al., JOURNAL OF CHROMATOGRAPHY B: BIOMEDICAL SCIENCES AND APPLICATIONS 703(1-2):225-33 (1997)). Optimized hydrogel formulations that demonstrate the desired two phase release kinetics are selected and explored in vivo.

Example 5

In Vitro Release Kinetics of Lcn2 Hydrogel

Figure 8:
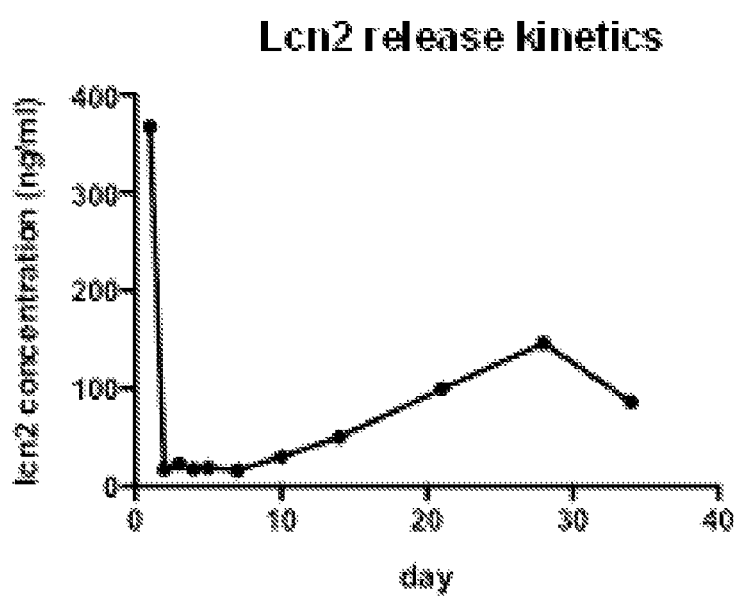
FIG. 8: The concentration of lipocalin-2 released from a lipocalin-2-hydrogel formulation was measured over the course of 35 days. The hydrogel formulation exhibited sustained release of lipocalin-2 over the entire study period.

The release kinetics of the Lcn2-hydrogel formulation were evaluated to verify that the hydrogel was capable of releasing Lcn2 in a sustained and continuous manner. 20 µg of Lcn2 was incorporated into the hydrogel and incubated at 37° C. for 35 days in sterile PBS buffer. Each day, 100 µl of PBS was collected. At the end of the release study period an ELISA was performed to determine the levels of released Lcn2. The Lcn2 ELISA assay was performed using the human Lipocalin/NGAL DuoSet (R&D SYSTEMS) according to the manufacturer's instructions. A 96-well ELISA microplate was coated with the Lcn2 capture antibody which was subsequently blocked with 1% BSA. Supernatants were applied to the microplate wells at 1:5 dilution. Positive signal was detected using the provided detection antibody and substrate solution (R&D SYSTEMS) at 450 nm. The hydrogel formulation exhibited sustained release of Lcn2 for at least 35 days (FIG. 8).

Example 6

Human Glioblastoma Stem Cells Migrate Towards the Lcn2 Hydrogels in Ex Vivo Brain Tissue Slices An ex vivo model for human glioblastoma was used to demonstrate the efficiency of the Lcn2 hydrogel in attracting migrating glioblastoma cells. Organotypic rat brain slices were prepared and implanted with 50,000 human GSCs using a Hamilton syringe. At the contralateral hemisphere, a hydrogel disc with Lcn2 (or PBS as control) was embedded. The slices were incubated at 37° C. in a $CO_2$ incubator for 7 days and then fixed and stained using a mouse monoclonal anti-human specific mitochondrial antibody MTCO2 (AB-CAM). The 1 mm thick organotypic cultures were fixed with a solution of 4% PFA in PBS, overnight at 4° C. After two washes with PBS, acetone permeabilization was performed for 3 minutes at −20° C. After two more washes with PBS, the tissue was blocked with 10% horse serum in TBS, for 1 hour at room temperature. Next, the tissue was incubated with the anti-mitochondrial antibody overnight at 4° C. at a 1:100 dilution in blocking buffer. After three washes with TBS, tissues were incubated with a donkey anti-mouse A488 (green) antibody, 1:1000 dilution (JACKSON LABORA- TORIES) for 3 hours at room temperature. Finally, tissues were mounted in concave slides using Vectashield (VECTOR) with DAPI.

Figure 9A:
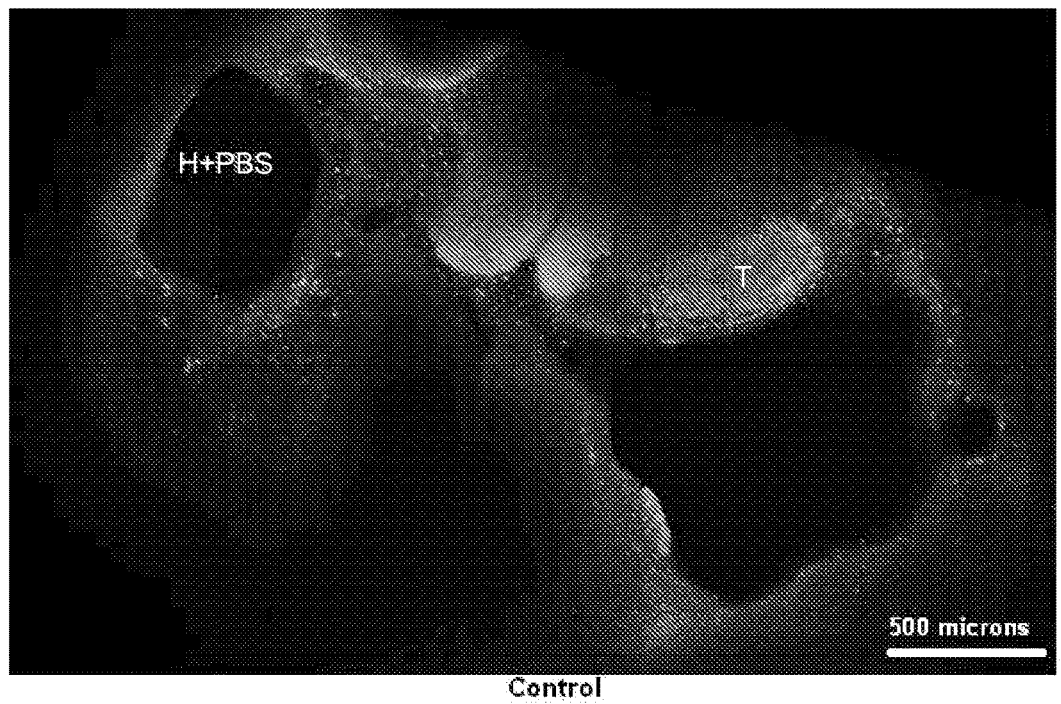
FIGS. 9A-C: Organotypic rat brain slices were implanted with human glioblastoma stem cells in order to provide an ex vivo model for human glioblastoma. A lipocalin-2-hydrogel disc was placed in the contralateral hemisphere. After incubation, fixing, and staining, it was observed that glioblastoma cells migrated from the "tumor site" (T) to the hydrogel site (H) (B, C). Control brain slices where PBS-hydrogel discs were placed in the contralateral hemisphere showed migration of glioblastoma cells throughout the slice without any directionality (A).
Figure 9B:
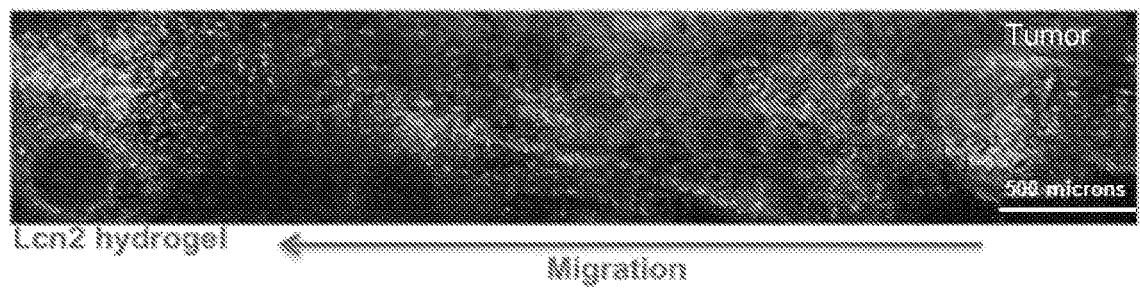
Figure 9C:
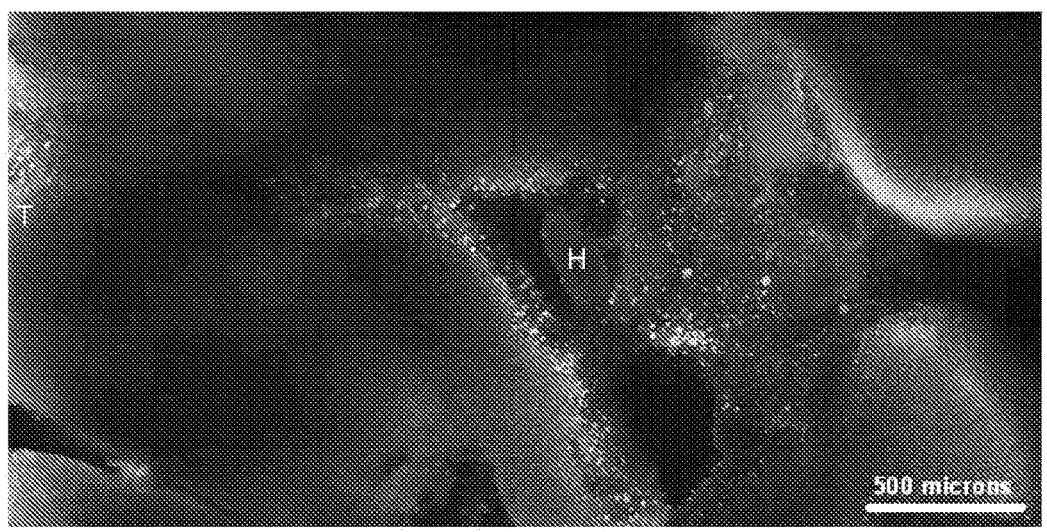

The Lcn2 hydrogels induced directed migration of glioblastoma cells from the tumor site (T) to the hydrogel (H) (FIGS. 9B and 9C—two independent GSCs). On the contrary, control slices with hydrogel and PBS showed extensive migration of glioblastoma cells over the whole slice without any directionality (FIG. 9A). The data suggested that Lcn2 diffuses from the hydrogel creating a gradient within the brain slice such that the migrating glioblastoma cells sense and follow the gradient to the hydrogel source.

Example 7

Figure 10A:
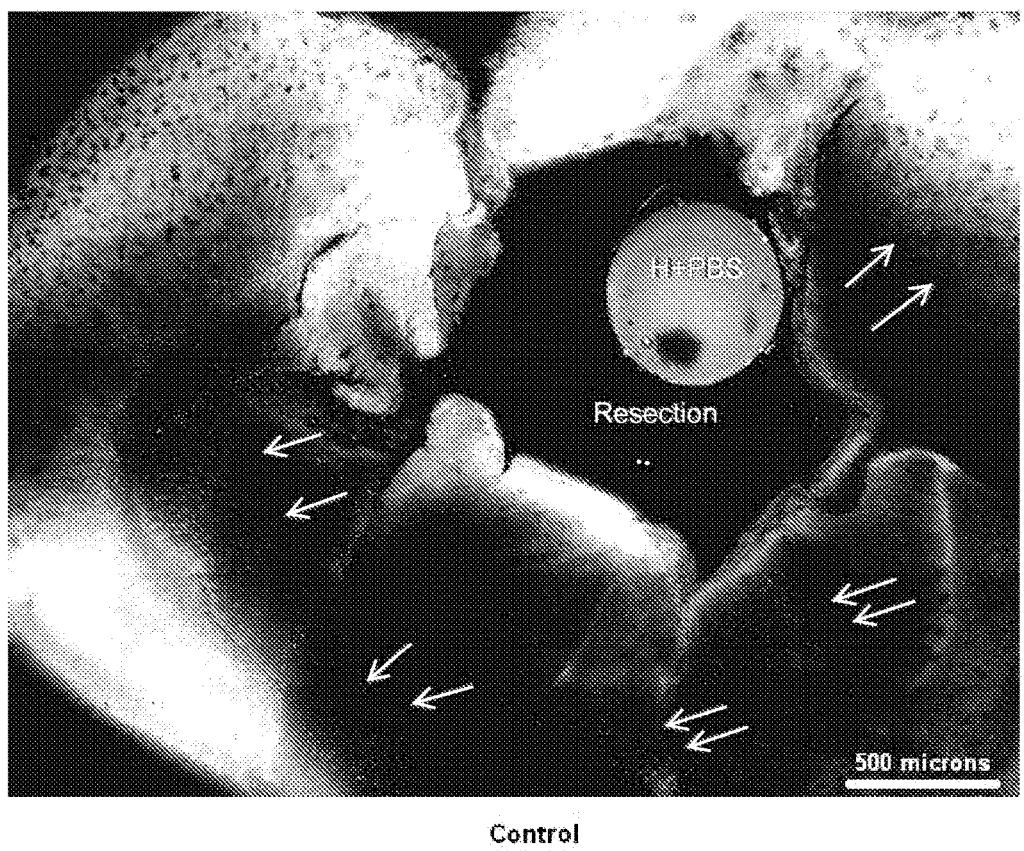
FIGS. 10A-B: Human glioblastoma stem cells were implanted into rat brain slices and the subsequent tumor was resected to provide an ex vivo model for resected human glioblastoma. A lipocalin-2-hydrogel disc was placed within the resection cavity and the brain slices were incubated, fixed, and stained. It was observed that glioblastoma cells migrated back to the vicinity of the resection cavity (B). Control brain slices where PBS-hydrogel discs were placed in the resection cavity showed migration of glioblastoma cells throughout the brain parenchyma (A)
Figure 10B:
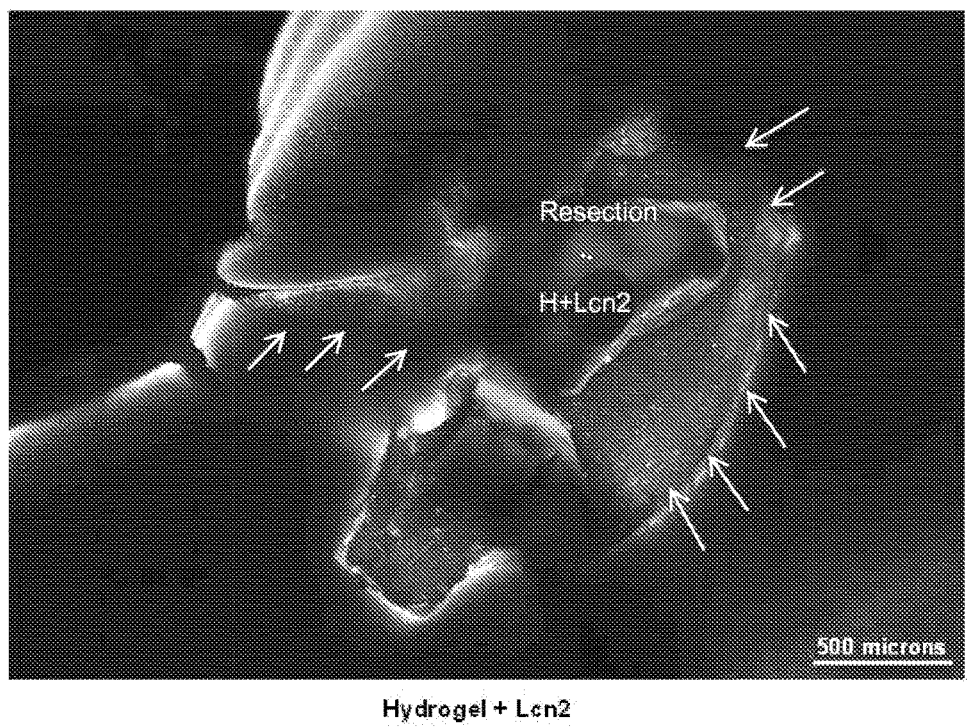

Lcn2 Hydrogels Attract the Migrating Glioblastoma Cells Back at the Side of Tumor Resection Human glioblastoma cells were implanted in a rat brain slice, cultured, and then incubated for 5 days to allow for the GSCs to migrate in the brain parenchyma. The tumor was microscopically resected creating a cavity in the brain parenchyma, which recapitulates the surgical resection process in humans. A Lcn2 hydrogel disc (or PBS control hydrogel disc) was placed within the cavity and incubated for an additional 5 days. The rat brain slices were fixed and stained for the human mitochondrial marker to detect and localize the topology of human GSCs within the organotypic culture. The Lcn2 hydrogel attracted the GSCs back to the vicinity of the resection cavity as opposed to the control culture where the GSCs were migrating throughout the brain parenchyma (FIGS. 10A and 10B).

Example 8

In Vivo Validation of Lipocalin-2 Hydrogel

In the absence of a spontaneous animal model for glioblastoma, intracranial injection of GFP-expressing human glioblastoma stem cells (hGSCs) into nude mice is performed, as this best recapitulates the invasive human histopathology (Lee et al., CANCER CELL 9(5):391-403 (2006)). A second surgery is then performed during which the stereotactic site of the initial tumor implantation will "resected" via aspiration. Following the creation of a resection cavity, the dual release lipocalin-2 (Lcn2)—temozolomide hydrogel is delivered. Control experiments delivering a hydrogel carrying Lcn2 alone, a hydrogel carrying temozolomide alone, a hydrogel alone, PBS alone, Lcn2 alone, or temozolomide alone are also performed. Ten animals are used for each treatment group and the experiment is repeated. To perform this experiment, a KOPF INSTRUMENTS stereotactic head frame immobilizes the rodent calvarium setting the bregma and lambda in the same plane. Sharp dissection exposes the underlying skull at a position 2 mm anterior and 2 mm lateral to the bregma (Yamada et al., THE TOKAI JOURNAL OF EXPERIMENTAL AND CLINICAL MEDICINE 29(4):167-73 (2004)). Transcalvarial access is gained by motorized drill. A Hamilton syringe with a 33 gauge needle is advanced to its target 3 mm below the skull. A low flow rate of injection is achieved by employing a stepping motor; allowing for 2 µl containing 10,000 hGSCs to be infused over 20 minutes. Bone wax seals the burr-hole.

Two weeks following surgery, animals return for stereotactic "resection"/aspiration surgery. Identical coordinates guide replacement of a Hamilton syringe with a 26 gauge, point style 5 needle to the original injection coordinates. Aspiration is carried out by reversing the stepping motor and withdrawing 4 µl volume over 20 minutes. This is followed by the placement of a new Hamilton 33 gauge needle syringe loaded to deliver 2 µl of therapeutic hydrogel or control agents over a period of 15 minutes. Bone wax reseals the burr-hole. To visualize the effect of the treatment on hGSC migration, post mortem immunofluorescence microscopy is performed every week for four weeks following the implantation of the hydrogel.

Example 9

Human Glioblastoma Cells Express Lcn2 Receptor

Figure 7:
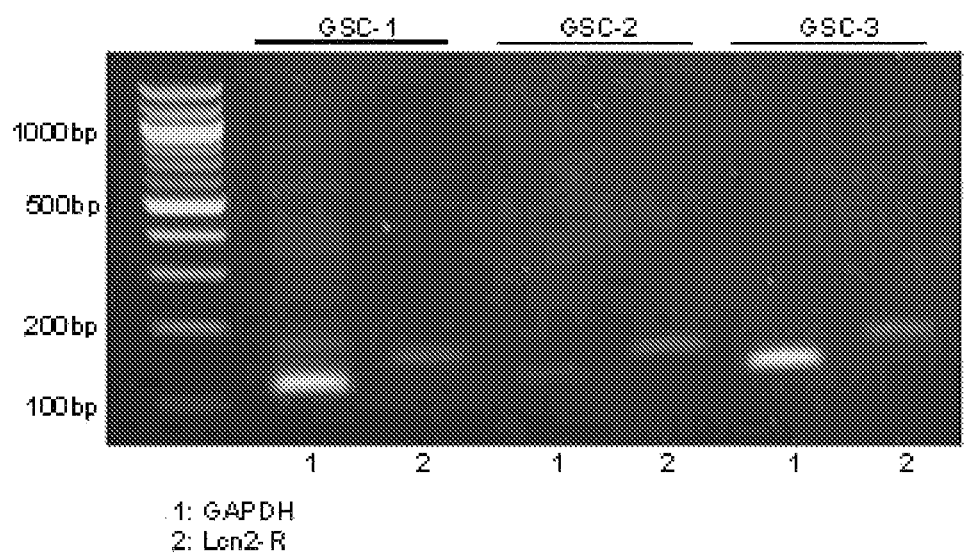
FIG. 7: Primers were designed to target the human homolog of Megalin (SEQ ID NOs: 3 and 4). After RNA extraction from three glioblastoma cells GSC-1, GSC-2, and GSC-3 (representing different subtypes of glioblastomas), RT-PCR was performed. PCR products were separated on a 2% agarose gel. Lipocalin-2 receptor DNA was observed for all three glioblastoma cell subtypes

In order to determine if human glioblastoma cells express a specific receptor for Lcn2 (Lcn-2), primers were generated for the human homolog of Megalin. The sequences of the primers were: AAATTGAGCACAGCACCTTTGA (forward primer; SEQ ID NO: 3), TCTGCTTTCCTGACTCGAATAATG (reverse primer; SEQ ID NO: 4). RNA was isolated from three glioblastoma cells (representing different subtypes of glioblastomas) using the PureLink™ RNA Mini KIT (LIFE TECHNOLOGIES) according to the manufacturer's protocol. RT-PCR was performed to detect the presence of LcnR-2 DNA. The PCR amplification protocol included an initial step of incubation at 94° C. for 10 minutes, followed by 40 cycles of: 15 seconds at 94° C., 30 seconds at 62° C., and 1 minute at 72° C., using TaKaRa Ex Taq (TAKARA). PCR amplified samples were separated on a 2% agarose gel with a 100 bp DNA ladder as a size marker (NEW ENGLAND BIOLABS). All three glioblastoma cell subtypes were shown to express Lcn2-R, explaining their positive response to Lcn2 chemoattraction (FIG. 7).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given composition or method unless indicated to the contrary or otherwise evident from the context.

It is noted that the terms "comprising" and "containing" are intended to be open and permit the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments.

This application refers to various issued patents, published patent applications, journal articles, and other publications, all of which are incorporated herein by reference in their entireties for all purposes. If there is a conflict between any of the incorporated references and the instant specification, the specification shall control.

While the present compositions and methods have been described with reference to preferred embodiments, these are to be regarded as illustrative rather than limiting. The compositions and methods to be protected are defined by the following claims.

What is claimed is:

1. A composition comprising:
   a chemoattractant; and
   a chemotherapeutic agent,
   wherein the composition is formulated in a matter such that the chemotherapeutic agent is released after the release of the chemoattractant, and wherein the chemoattractant is selected from the group consisting of lipocalin-2, epidermal growth factor, CSF-1, CCLx, ETs 1-2, Lps, SDF-1, HGF, PDGF, BIB, FGF-1, VEGF-α, Heregulin, TGF-α, and fetal serum.

2. The composition of claim 1, wherein said composition is formulated to be implanted in a subject in need thereof.

3. The composition of claim 1, wherein said chemotherapeutic agent is selected from the group consisting of temozolomide, cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, folinic acid, and oxaliplatin.

4. The composition of claim 3, wherein the temozolomide is present in an amount of about 200 mg/m$^2$.

5. The composition of claim 1, wherein said chemoattractant attracts brain cancer cells.

6. The composition of claim 1, wherein said chemoattractant is lipocalin-2.

7. The composition of claim 6, wherein said lipocalin-2 has the amino acid sequence of SEQ ID NO:1.

8. The composition of claim 1, wherein the composition is formulated as a biodegradable biphasic-release hydrogel.

9. The composition of claim 8, wherein said hydrogel comprises two multifunctional polyols that possess thiol functionality and one multifunctional polyol that contains acrylate functionality.

10. A method for attracting and trapping cancer cells comprising: implanting a composition comprising a chemoattractant and a chemotherapeutic agent into a subject in need thereof; wherein the chemotherapeutic agent is released from the composition after the release of the chemoattractant, and wherein the chemoattractant is selected from the group consisting of lipocalin-2, epidermal growth factor, CSF-1, CCLx, ETs 1-2, LPs, SDF-1, HGF, PDGF BIB, FGF-1, VEGF-α, Heregulin, TGF-α, and fetal serum.

11. The method of claim 10, wherein said chemoattractant attracts brain cancer cells.

12. The method of claim 10, wherein said chemoattractant is lipocalin-2.

13. The method of claim 12, wherein said lipocalin-2 has the amino acid sequence of SEQ ID NO:1.

14. The method of claim 10, wherein said composition is selected from the group consisting of a biodegradable hydrogel, a biodegradable scaffold, a biodegradable polymer microsphere, and mixtures thereof.

15. The method of claim 10, wherein said composition is an implantable drug delivery pump.

16. The method of claim 10, wherein the chemoattractant is present in an amount of between about 0.5 mg to 5 mg.

17. The method of claim 10, wherein chemoattractant is released for approximately 1-2 weeks before the chemotherapeutic agent is released.

18. A method for treating cancer comprising:
   identifying a subject whose cancer cells express a lipocalin-2 receptor; and
   implanting an effective amount of the composition of claim 1 into a subject need thereof.

* * * * *